United States Patent
Dalal et al.

(10) Patent No.: US 9,943,234 B2
(45) Date of Patent: Apr. 17, 2018

(54) USING RESPIRATION DISTRESS MANIFESTATIONS FOR HEART FAILURE DETECTION

(75) Inventors: Yousufali Dalal, St. Louis Park, MN (US); John D. Hatlestad, Maplewood, MN (US); Yi Zhang, Blaine, MN (US); Aaron Lewicke, Forest Lake, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2733 days.

(21) Appl. No.: 11/736,058

(22) Filed: Apr. 17, 2007

(65) Prior Publication Data

US 2008/0262360 A1   Oct. 23, 2008

(51) Int. Cl.
*A61B 5/08* (2006.01)
*A61B 5/0205* (2006.01)
(Continued)

(52) U.S. Cl.
CPC .......... *A61B 5/0205* (2013.01); *A61B 5/1116* (2013.01); *A61B 5/4818* (2013.01);
(Continued)

(58) Field of Classification Search
USPC .................................... 600/536, 534; 607/17
See application file for complete search history.

(56) References Cited

U.S. PATENT DOCUMENTS

| 6,678,547 B2 | 1/2004 | Carlson et al. |
| 6,714,813 B2 | 3/2004 | Ishigooka et al. |

(Continued)

FOREIGN PATENT DOCUMENTS

| CN | 200880020517.X | 10/2012 |
| EP | 1582233 A2 | 10/2008 |

(Continued)

OTHER PUBLICATIONS

Banyai, Paroxysmal Nocturnal Dyspnea, 1972, Chest, 61(3), 220.*
(Continued)

*Primary Examiner* — Tiffany Weston
*Assistant Examiner* — Tho Tran
(74) *Attorney, Agent, or Firm* — Schwegman Lundberg & Woessner, P.A.

(57) ABSTRACT

Systems and methods for diagnosing one or more respiration distress manifestations by implantably recognizing their occurrence and evaluating information about the same to provide an indication of present or impending worsening heart failure are discussed. Using information produced by an implantable respiration sensor circuit and an implantable physiological sensor circuit, such as at least one of a physical activity sensor circuit or a posture sensor circuit, an implantable or external processor circuit may detect a respiration disturbance and an associated subsequent arousal from stable state occurrence and thereafter evaluate over time arousal from stable state occurrences to provide the indication of present or impending worsening heart failure. In one example, information about a fluid level within a subject is used in determining the indication of worsening heart failure. In various examples, a regimen is initiated or adjusted in response to the indication of present or impending worsening heart failure.

20 Claims, 5 Drawing Sheets

(51) Int. Cl.
  *A61B 5/11* (2006.01)
  *A61B 5/00* (2006.01)
  *A61N 1/362* (2006.01)

(52) U.S. Cl.
  CPC .......... *A61N 1/3627* (2013.01); *A61B 5/0816* (2013.01); *A61B 5/686* (2013.01)

(56) References Cited

U.S. PATENT DOCUMENTS

| | | |
|---|---|---|
| 7,127,290 B2 | 10/2006 | Girouard et al. |
| 7,226,422 B2 | 6/2007 | Hatlestad et al. |
| 2003/0055461 A1* | 3/2003 | Girouard et al. ............... 607/17 |
| 2005/0085738 A1* | 4/2005 | Stahmann et al. ............ 600/529 |
| 2006/0243281 A1 | 11/2006 | Berthon-Jones |
| 2007/0021678 A1 | 1/2007 | Beck et al. |
| 2007/0106130 A1 | 5/2007 | Hatlestsad et al. |
| 2007/0118183 A1* | 5/2007 | Gelfand et al. ................. 607/42 |
| 2007/0213621 A1 | 9/2007 | Reisfeld et al. |
| 2007/0270707 A1 | 11/2007 | Belalcazar |
| 2008/0033304 A1 | 2/2008 | Dalal et al. |
| 2008/0039730 A1 | 2/2008 | Pu et al. |

FOREIGN PATENT DOCUMENTS

| | | |
|---|---|---|
| WO | WO-2005/018737 A1 | 3/2005 |
| WO | WO-2006/082589 A2 | 8/2008 |
| WO | WO-2008/130549 A1 | 10/2008 |

OTHER PUBLICATIONS

"Australian Application Serial No. 2008241524, First Examiner Report dated Jan. 10, 2011", 2 Pgs.

"European Application Serial No. 08754088.6, Communication dated Jun. 21, 2010", 4 pgs.

Jimison, H. B., et al., "Monitoring of Body Weight for Heart Failure Patients: Variability of Weight and Self-Reporting", *Proceedings of the 25th Annual International Conference of the IEEE EMBS*, (2003), 3665-3668.

"International Application Serial No. PCT/US2008/004858, International Search Report dated Jul. 18, 2008", 5 pgs.

"International Application Serial No. PCT/US2008/004858, Written Opinion dated Jul. 18, 2008", 6 pgs.

Belalcazar, Andres , "Monitoring Fluid in a Subject Using a Weight Scale", U.S. Appl. No. 11/419,120, filed May 18, 2006.

Hatlestad, J. D., et al., "Physiological Response to Posture Change", U.S. Appl. No. 11/466,925, filed Aug. 24, 2006, 21 Pages.

Pu, Yachuan , et al., "Respiration Monitoring for Heart Failure Using Implantable Device", U.S. Appl. No. 11/463,076, filed Aug. 8, 2006, 30 Pages.

Schiff, G. D., et al., "Decompensated heart failure: symptoms, patterns of onset, and contributing factors.", *Am J Med.*, 114(8), (2003), 625-30.

Yousufali, Dalal , et al., "Sleep State Detection", U.S. Appl. No. 11/458,602, filed Jul. 19, 2006, 32 Pages.

"European Application Serial No. 08754088.6, Response filed Dec. 1, 2010 to Office Action dated Jun. 21, 2010", 16 pgs.

"Japanese Application Serial No. 2010-504067, Voluntary Amendment filed Oct. 22, 2009", 32 pgs.

"Australian Application Serial No. 2008241524, Response filed Jul. 15, 2011 to Examiner Report dated Jan. 10, 2011", 19.

"Chinese Application Serial No. 200880020517.X, Office Action dated May 27, 2011", 11.

"European Application Serial No. 08754088.6, Examination Notification Art. 94(3) dated Aug. 7, 1012", 4 pgs.

"European Application Serial No. 08754088.6, Summons to Attend Oral Proceeding dated Apr. 9, 2013", 4 pgs.

"Japanese Application No. 2010-504067, Response filed Jun. 17, 2013 to Non Final Office Action dated Mar. 19, 2013", With English Claims, 11.

"Japanese Application Serial No. 2010-504067, Non Final Office Action dated Mar. 19, 2013", With English Translation, 9.

* cited by examiner

USING RESPIRATION DISTRESS MANIFESTATIONS FOR HEART FAILURE DETECTION

TECHNICAL FIELD

This patent document pertains generally to medical systems and methods. More particularly, but not by way of limitation, this patent document pertains to medical systems and methods using an objective diagnosis of one or more respiration distress manifestations for heart failure detection.

BACKGROUND

Congestive heart failure, or simply heart failure, is a condition in which a subject's heart can't pump the needed amount of blood to the subject's other organs causing fluid to build-up behind the heart. Congestive heart failure can be conceptualized as an enlarged weakened heart muscle, which results in poor cardiac output. As blood flow out of the heart is reduced, blood returning to the heart through the veins backs up, causing congestion in bodily tissues. This congestion may cause swelling in the legs, ankles, or other parts of the body and may also result in fluid collecting in, or flowing to, the subject's thorax. Thus, congestion may be associated with heart failure.

OVERVIEW

Congestion may be manifested in a heart failure subject's body in several ways. One condition highly correlated with congestion is respiratory distress, especially when the subject assumes a recumbent position. Congestion often results in the lungs becoming partially filled with fluid once the subject lies down, and as a result, the lungs maintain the partially filled state until the subject moves to an upright position. This filling becomes a barrier to normal gas (i.e., oxygen and carbon-dioxide) exchange and results in the subject having difficulty in breathing. For this reason, respiratory distress may provide a good indication of congestion. Unfortunately, many manifestations of respiratory distress, and thus congestion, are not timely detectable.

The present inventors have recognized that one problem presented by heart failure subjects is timely detection and treatment of heart failure before an advanced disease stage is reached. To this end, the present inventors have recognized that there exists an unmet need for systems and methods configured for objectively diagnosing certain respiration distress manifestations, which may provide a timely detection of heart failure.

Accordingly, this patent document discusses, among other things, systems and methods for diagnosing one or more respiration distress manifestations by implantably recognizing their occurrence and evaluating information about the same to provide an indication of present or impending worsening heart failure. Using information produced by an implantable respiration sensor circuit and an implantable physiological sensor circuit, such as at least one of a physical activity sensor circuit or a posture sensor circuit, an implantable or external processor circuit may detect a respiration disturbance and an associated subsequent arousal from stable state occurrence and thereafter evaluate over time arousal from stable state occurrences to provide the indication of present or impending worsening heart failure. In one example, information about a fluid level within a subject is used in determining the indication of worsening heart failure. In various examples, a regimen is initiated or adjusted in response to the indication of present or impending worsening heart failure.

In Example 1, a system comprises an implantable medical device including a respiration sensor circuit configured for producing a respiration signal indicative of a respiration or a respiration related parameter of a subject, and a physiological sensor circuit that includes at least one of a physical activity sensor circuit configured for producing a physical activity signal indicative of a physical activity level of the subject or a posture sensor circuit configured for producing a posture signal indicative of a posture of the subject. The system further comprises an implantable or external processor circuit including an input to receive information about the respiration signal and at least one of the physical activity signal or the posture signal, the processor circuit configured for detecting a respiration disturbance using the respiration signal and configured for detecting an associated subsequent arousal from stable state occurrence from at least one of the physical activity signal or the posture signal, the processor circuit further configured for evaluating over time, at least in part, arousal from stable state occurrences for providing an indication of present or impending worsening heart failure.

In Example 2, the system of Example 1 optionally comprises a clock circuit configured for producing at least one timestamp associated with at least one of the respiration signal, the physical activity signal, or the posture signal.

In Example 3, the system of Example 2 optionally comprises a memory configured for storing information about the timestamp and at least one of the respiration signal, the physical activity signal, or the posture signal with which the timestamp is associated.

In Example 4, the system of at least one of Examples 1-3 optionally comprises a regimen control circuit configured for adjusting a regimen provided to the subject using, at least in part, information about at least one of the detected respiration disturbance, the detected arousal from stable state occurrence, or the indication of present or impending worsening heart failure.

In Example 5, the system of at least one of Examples 1-4 optionally comprises an external user-interface device communicatively coupled to the implantable medical device and including a user-detectable indication of an evaluation over time of at least one of the respiration disturbance, the arousal from stable state occurrence, or the indication of present or impending worsening heart failure.

In Example 6, the system of Example 5 is optionally configured such that the external user-interface includes a user input device configured for receiving programming information from a user and communicating the programming information to the implantable medical device.

In Example 7, the system of at least one of Examples 1-6 optionally comprises a fluid detector circuit configured for producing an indication of a fluid level within the subject; and wherein the processor is configured to receive the indication of the fluid level for use in determining the indication of present or impending worsening heart failure.

In Example 8, the system of Example 7 is optionally configured such that the fluid detector circuit includes an external weight scale comprising a communication circuit configured for directly or indirectly communicating fluid level information to the processor circuit.

In Example 9, the system of at least one of Examples 1-8 optionally comprises a stable state detector including at least one of a sleep detector circuit configured for determining whether the subject is asleep or awake, the physical activity sensor, or the posture sensor.

In Example 10, the system of at least one of Examples 1-9 is optionally configured such that the respiration sensor circuit is configured to produce the respiration signal in response to a detected change in a fluid level within the subject.

In Example 11, the system of at least one of Examples 1-10 is optionally configured such that the respiration sensor circuit is configured to produce the respiration signal in response to a detected change in lung volume.

In Example 12, the system of at least one of Examples 1-11 is optionally configured such that the respiration sensor circuit is configured to produce the respiration signal in response to a detected change in respiration rate.

In Example 13, the system of at least one of Examples 1-12 is optionally configured such that the respiration signal produced by the respiration sensor circuit includes information about at least one of a respiration rate, a tidal volume, a heart rate, or a heart rate variability.

In Example 14, the system of at least one of Examples 1-13 is optionally configured such that the physical activity sensor circuit is configured to produce the physical activity signal in response to a detected increase in the physical activity level.

In Example 15, the system of at least one of Examples 1-14 is optionally configured such that the posture sensor circuit is configured to produce the posture signal in response to a detected change in the posture to a more upright position.

In Example 16, a method comprises implantably detecting a respiration disturbance followed by detecting an associated arousal from stable state occurrence, wherein detecting the arousal from stable state occurrence includes detecting information about at least one of a physical activity level or a posture of a subject; and determining an indication of present or impending worsening heart failure by evaluating over time, at least in part, arousal from stable state occurrences.

In Example 17, the method of Example 16 optionally comprises detecting a fluid accumulation within the subject and using information about the fluid accumulation in determining the indication of present or impending worsening heart failure.

In Example 18, the method of at least one of Examples 16-17 optionally comprises detecting a stable state, including detecting at least one of a stable sleep state, a stable physical activity level, or a stable posture position.

In Example 19, the method of at least one of Examples 16-18 optionally comprises evaluating over time a paroxysmal nocturnal dyspnea occurrence.

In Example 20, the method of Example 19 optionally comprises determining the indication of present or impending worsening heart failure by also detecting at least one of an apnea occurrence or a Cheyne-Stokes breathing occurrence.

In Example 21, the method of Example 20 is optionally configured such that determining the indication of present or impending worsening heart failure includes weighting the evaluation of at least one of the paroxysmal nocturnal dyspnea occurrence, the apnea occurrence, or the Cheyne-Stokes breathing occurrence.

In Example 22, the method of at least one of Examples 16-21 optionally comprises displaying a trending or counting of at least one of the respiration disturbance, the arousal from stable state occurrence, or the indication of present or impending worsening heart failure.

In Example 23, the method of at least one of Examples 16-22 optionally comprises initiating or adjusting a regimen in response to the indication of present or impending worsening heart failure.

In Example 24, the method of at least one of Examples 16-23 is optionally configured such that detecting the respiration disturbance includes detecting a lung volume oscillation and decay.

In Example 25, the method of at least one of Examples 16-24 is optionally configured such that detecting the respiration disturbance includes detecting an increase in respiration rate.

In Example 26, the method of at least one of Examples 16-25 is optionally configured such that detecting the respiration disturbance includes detecting an increase in heart rate or a change in heart rate variability.

In Example 27, the method of at least one of Examples 16-26 is optionally configured such that detecting the arousal from stable state includes detecting at least one of an increase in the physical activity level or a change in the posture to a more upright position.

Advantageously, the present systems and methods are applicable to all implantable medical devices (IMDs) with a respiration sensor circuit and a physiological sensor circuit, such as at least one of a physical activity sensor circuit or a posture sensor circuit. Using information gathered by these circuits, the present systems and methods are configured for objectively diagnosing respiration distress manifestations, such as one or more paroxysmal nocturnal dyspnea (PND) events, which are generally typified by a respiration disturbance followed by an associated arousal from stable state (e.g., sleep) occurrence. The present systems are further configured to evaluate, such as trend or count, over time at least one of the respiration disturbance or the associated subsequent arousal from stable state occurrence, such as to provide an indication of present or impending worsening heart failure. Using information about one or more PND events may advantageously provide a tool for early, and therefore actionable, detection to present or impending worsening heart failure.

These and other examples, advantages, and features of the present systems and methods will be set forth in part in the detailed description, which follows, and in part will become apparent to those skilled in the art by reference to the following description of the present systems, methods, and drawings or by practice of the same.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments discussed in this patent document.

DETAILED DESCRIPTION

Figure 1:
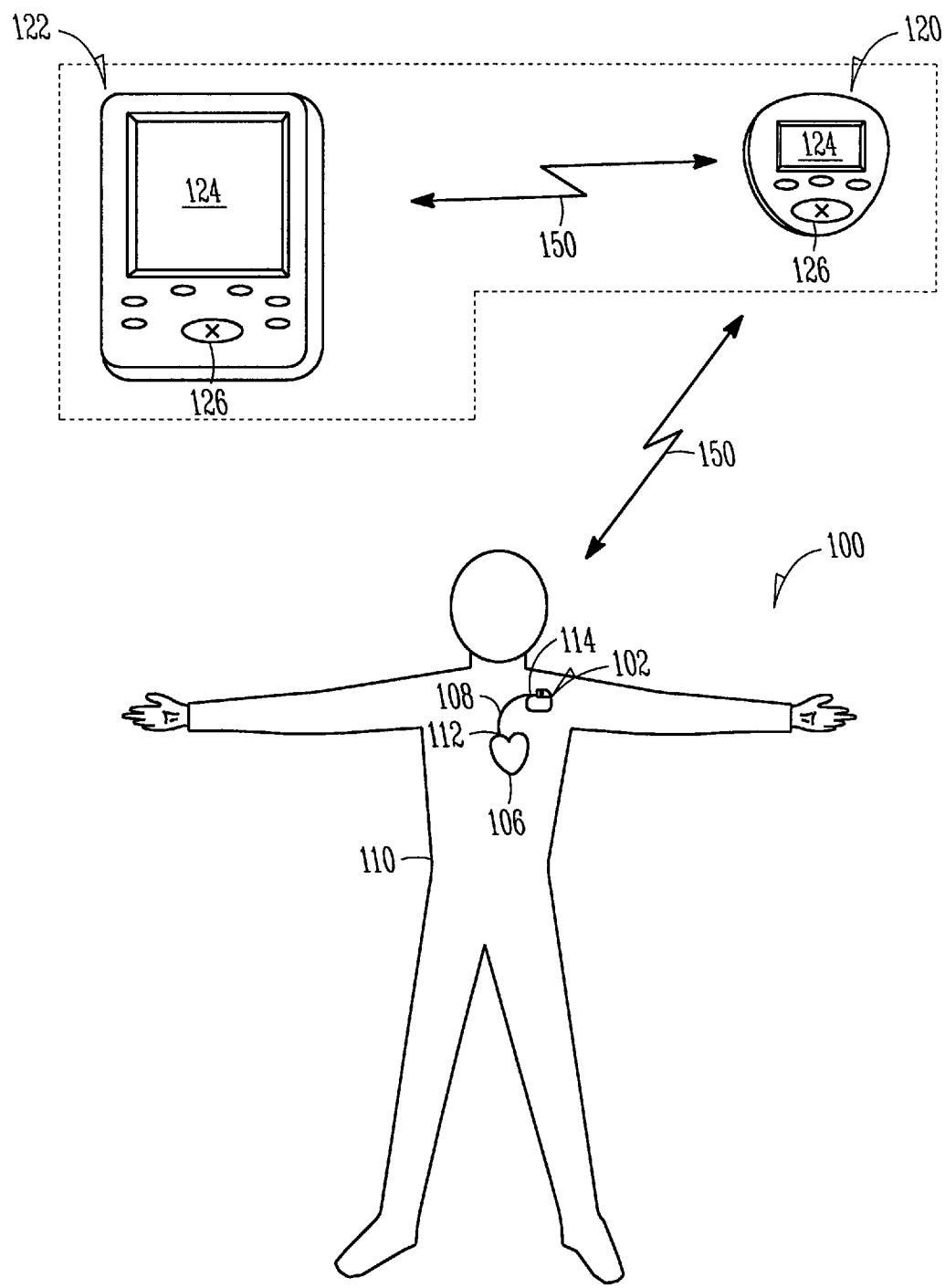
FIG. 1 is a schematic view illustrating one conceptual example of a system configured for objectively diagnosing one or more respiration distress manifestations, such as one or more PND events, and an environment in which the system may be used.

The following Detailed Description includes references to the accompanying drawings, which form a part hereof. The drawings show, by way of illustration, specific embodiments in which the present systems and methods may be practiced. It is submitted that these embodiments, which are also referred to herein as "examples," are described in enough detail to enable those skilled in the art to practice the present systems and methods. The embodiments may be combined, other embodiments may be utilized or structural, electrical, or logical changes may be made without departing from the scope of the present systems and methods. The following Detailed Description is, therefore, not to be taken in a limiting sense, and the scope of the present systems and methods is defined by the appended claims, along with the full scope of legal equivalents to which such claims are entitled.

In this document, the terms "a" or "an" are used to include one or more than one; the term "or" is used to refer to a nonexclusive "or" unless otherwise indicated; and the phrase "implantable medical device" or simply "IMD" is used to include, but is not limited to, implantable cardiac rhythm management (CRM) systems such as pacemakers, cardioverters/defibrillators, pacemakers/defibrillators, biventricular or other multi-site resynchronization or coordination devices such as cardiac resynchronization therapy (CRT) device, subject monitoring systems, neural modulation systems, and drug delivery systems. Additionally, it is to be understood that the phraseology or terminology employed herein, and not otherwise defined, is for the purpose of description only and not of limitation. Furthermore, all patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Introduction:

As discussed above, congestion may cause swelling in the legs, ankles, or other parts of the body and may also result in fluid collecting in, or flowing to, a subject's thorax, thereby becoming a barrier to normal gas exchange and causing respiration distress. The fluid build-up in the thorax may result in pulmonary edema (i.e., the build-up of extravascular fluid in the lungs) or pleural effusion (i.e., the build-up of extravascular fluid in the space between the lungs and the ribs). These conditions, if they exist, present medical emergencies that require immediate, and oftentimes challenging, care and can sometimes prove fatal. Thus, it is of great benefit to timely recognize and treat excessive fluid build-up within a subject. Unfortunately, the first indication that a subject's caregiver typically has of an occurrence of excessive internal fluid build-up is very late in the heart failure disease process, such as when it becomes a physical manifestation with swelling, noticeable weight gain, jugular venous distension, or breathing difficulties so overwhelming as to be noticed by the subject who then proceeds to be examined by his/her caregiver. For a heart failure subject, significant clinical intervention (e.g., hospitalization) at such a physically apparent time would likely be required.

A PND event (i.e., an event characterized by an arousal from sleep due to breathlessness caused when left ventricular dysfunction leads to pulmonary edema) is one manifestation of respiration distress and if diagnosed correctly, may provide a timely indication of heart failure before significant clinical intervention is needed. Unfortunately, current systems and methods for diagnosing PND events rely on the subjective determination of subjects who may not be conscious of the occurrence of a PND event, and who may feel they have been woken for reasons other than some form of breathlessness. This provides a challenge to caregivers as they currently have to rely on subject memory to make a positive diagnosis of a PND event, thereby delaying appropriate therapy or other action to counter the disorder or underlying disease.

Advantageously, the present system and methods provide for the objective diagnosis of one or more respiration distress manifestations, such as one or more PND events, by implantably recognizing their occurrence and evaluating over time information about the same to provide an indication of present or impending worsening heart failure. Using an implantable respiration sensor circuit, an implantable physiological sensor circuit, such as at least one of a physical activity sensor circuit or a posture sensor circuit, and optionally a fluid detector circuit, an apnea detector circuit, or a Cheyne-Stokes breathing detector circuit, PND events can be evaluated, such as trended or counted, over time for use as an indication of present or impending worsening heart failure. In various examples, a PND event is diagnosed when a stable state, such as a sleep state, a stable activity level, or a stable posture position has been detected followed by the detection of a respiration disturbance (e.g., an oscillation and decay of lung volume towards zero resulting in hypopnoea, apnea, rapid breathing or rapid shallow breathing) and an associated subsequent arousal from the stable state (e.g., an increase in a subject's physical activity level or a move by the subject to a more upright posture position), as will be further discussed below.

Examples:

FIG. 1 is a schematic drawing illustrating generally, by way of example, but not by way of limitation, one embodiment of a system 100 and an environment in which the system 100 is used. In varying examples, the system 100 is configured for objectively diagnosing one or more respiration distress manifestations, such as one or more PND events, in a subject 110. The system 100 may further be configured for evaluating, such as trending or counting, over time the detected PND events for use, at least in part, as an indication of present or impending worsening heart failure or a stimulus for regimen (e.g., therapy) intervention. In some examples, the system 100 may be configured to determine an efficacy of the regimen intervention. In this way, present or impending worsening heart failure may be earlier detected and acted upon than is currently possible.

In FIG. 1, the system 100 includes an IMD 102, such as a CRM device, which is coupled via an electrode bearing lead 108 to a heart 106 of the subject 110. The system 100 also includes one or more programmers or other external user-interface devices 120, 122 providing wireless communication with the IMD 102 or one another, such as by using telemetry 150 or other known communication techniques. As shown, the external user-interface devices 120, 122 include a user-detectable indication 124, such as an LCD or LED display, for textually or graphically (e.g., via a counter or line graph depicted over a period of time) relaying information about one or more respiration distress manifestations, such as PND trended or counted information, to the subject 110 or his/her caregiver. Additionally or alternatively, the external user-interface devices 120, 122 include a user input device 126 configured for receiving programming information from a user (e.g., the subject 110 or his/her caregiver) and communicating such programming information to the IMD 102.

The lead 108 includes a proximal end 114, which is coupled to the IMD 102, and a distal end 112, which is coupled on or about one or more portions of the heart 106. The distal end 112 of the lead 108 generally includes, among other things, one or more pacing or defibrillation electrodes for providing pacing, resynchronization, cardioversion, or defibrillation regimen therapy to the heart 106 or neuromodulation of one or more nerves within the subject 110.

Figure 2:
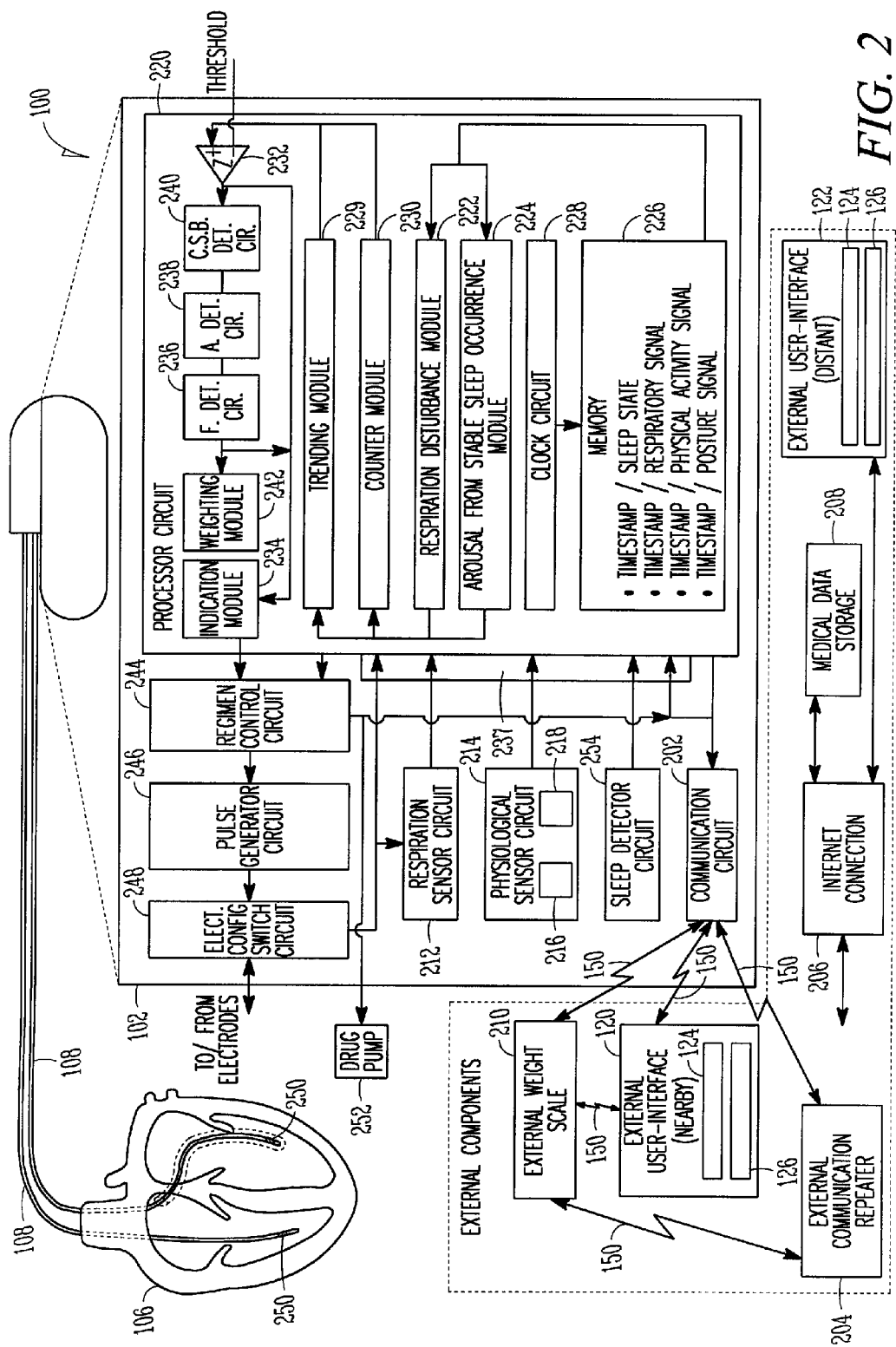
FIG. 2 is a block diagram illustrating one conceptual example of a system configured for objectively diagnosing one or more respiration distress manifestations, such as one or more PND events.

FIG. 2 is a block diagram illustrating generally, by way of example, but not by way of limitation, one conceptual example of a system 100 configured for objectively diagnosing one or more respiration distress manifestations, such as one or more PND events. In this example, the system 100 includes a hermetically sealed IMD 102 coupled to a heart 106 by one or more electrode-bearing leads 108 and one or more programmers or other external user-interface devices 120 (nearby), 122 (distant).

As shown, the IMD 102 carries various electrical components, such as a communication circuit 202, which is configured for wirelessly communicating with a communication circuit of the nearby external user-interface device 120. In certain examples, the communication circuit 202 is configured for wirelessly communicating with a communication circuit of a distant external user-interface device 122, such as by using a nearby external communication repeater 204. In one such example, the external communication repeater 204 is coupled to the distant external user-interface device 122 via an Internet/phone connection 206. The Internet/phone connection 206, in certain examples, allows the external communication repeater 204 to couple with an electronic medical data storage 208. In a further example, the communication circuit 202 of the IMD 102 is communicatively coupled to a communication circuit of an external weight scale 210 or other external fluid detection sensor, the latter of which may also be communicatively coupled to the communication circuits of the external user-interface devices 120, 122. One example of a suitable external weight scale 210 is described in commonly-owned Belalcazar, U.S. patent application Ser. No. 11/419,120, entitled "MONITORING FLUID IN A SUBJECT USING A WEIGHT SCALE," which is incorporated herein by reference in its entirety, including its description of an external weight scale and using the external weight scale to determine a fluid level within the subject. In addition or in the alternative to the external fluid detection sensor, an internal fluid detector circuit may also be used to provide an indication of a fluid level within the subject. In one example, the external fluid detection sensor or the internal fluid detector circuit is used to provide an indication of a peripheral edema level with the subject. As discussed above, peripheral edema (e.g., swelling in the legs, ankles, or other parts of the body) may result in fluid collecting in, or flowing to, a subject's thorax leading to pulmonary edema or pleural effusion and ultimately, respiration distress manifestations such as one or more PND events. Thus, fluid detector circuits can aid in the objective diagnosis of respiration distress manifestations.

PND events are marked by waking or transitory episodes from a stable state, such as stable sleep, a stable physical activity level, or a stable posture position. It is for this reason that in various examples, the IMD 102 includes a sleep detector circuit 254 configured for determining whether the subject 110 (FIG. 1) is asleep or awake. One example of a suitable sleep detector circuit 254 is described in commonly-owned Carlson et al., U.S. patent application Ser. No. 09/802,316, entitled "CARDIAC RHYTHM MANAGEMENT SYSTEM USING TIME-DOMAIN HEART RATE VARIABILITY INDICIA," which is incorporated herein by reference in its entirety, including its description of a sleep detector circuit. In various examples, the IMD 102 additionally includes two or more sensor circuits, such as a respiration sensor circuit 212 and a physiological sensor circuit 214, therewithin or implanted nearby and coupled thereto. The respiration sensor circuit 212 is configured for producing a respiration signal indicative of a respiration or a respiration related parameter (e.g., a respiration rate, a tidal volume, a heart rate, or a heart rate variability) of the subject 110. The physiological sensor circuit 214 includes at least one of a physical activity sensor circuit 216 configured for producing a physical activity signal indicative of a physical activity level of the subject 110 or a posture sensor circuit 218 configured for producing a posture signal indicative of a posture of the subject 110.

An implantable or external processor circuit 220 includes one or more inputs 237 to receive information about the respiration signal, at least one of the physical activity signal or the posture signal, and the sleep state information detected by the sleep detector circuit 254. In various examples, the processor circuit 220 includes a respiration disturbance module 222 to detect a respiration disturbance using the respiration signal and an arousal from stable state occurrence module 224 to detect an associated subsequent arousal from stable state occurrence from at least one of the physical activity signal, the posture signal, or the sleep state information. In this example, an on-board memory 226 stores information about at least one of the respiration signal, the physical activity signal, the posture signal, or the sleep state information along with a timestamp associated with such signals. Additionally, in various examples, the on-board memory 226 may receive and store the programming of the IMD 102, which is utilized by the processor circuit 220 when implementing the necessary logic operations of the system 100. In one example, the timestamp is produced by a clock circuit 228 in communication with the memory 226.

In various examples, the processor circuit 220 further includes at least one evaluation module, such as a trending module 229 or a counter module 230, which are respectively configured to trend information about, or count the prevalence over time of, one or both of the respiration disturbance or the associated subsequent arousal from stable state occurrence for use in providing an indication of present or impending worsening heart failure. In this example, the trended or counted respiration or arousal data is input to a comparator 232, which compares the data to a specified threshold that is also input to the comparator 232. If it is found that the input data exhibits a characteristic of present or impending worsening heart failure or is otherwise significant, the resulting comparison may be input to a present or impending disease state indication module 234 where it is optionally combined and processed with other information indicative of present or impending worsening heart failure, such as information about at least one of fluid accumulation within the subject 110, an apnea occurrence, or a Cheyne-Stokes breathing occurrence.

As shown in FIG. 2, at least one of a fluid detector circuit 236, an apnea detector circuit 238, or a Cheyne-Stokes breathing detector circuit 240 may be provided for respectively producing the information about the fluid accumulation within the subject 110, the apnea occurrence, or the Cheyne-Stokes breathing occurrence. In various examples, the information about the fluid accumulation within the subject 110 includes information about the presence or absence of pulmonary edema (i.e., fluid retention in the thoracic cavity) or peripheral edema (i.e., fluid retention in the extremities), both of which, if present, may correlate to a positive indication of present or impending worsening heart failure. In various examples, the information about the apnea or Cheyne-Stokes breathing occurrence(s) includes the present, absence, or prevalence of such events. The presence of one or more apnea or Cheyne-Stokes breathing occurrences may correlate to a positive indication of present or impending worsening heart failure. One example of a suitable apnea detector circuit 238 is described in commonly-owned Dalal et al., U.S. patent application Ser. No. 11/458,602, entitled "SLEEP STATE DETECTION," which is incorporated herein by reference in its entirety, including its description of determining apnea and hypopnea events.

A weighting module 242 including various weights (e.g., Weight 1, Weight 2, ..., Weight N) may further be used in conjunction with some combination of the evaluated, such as trended or counted, respiration or arousal data, the fluid accumulation information, the apnea occurrence information, or the Cheyne-Stokes breathing occurrence information to arrive at the indication or present or impending worsening heart failure. In certain examples, a numerically different weight corresponds to each type of information detected, such that the numerically greatest weight corresponds to the type of information detected which points towards the greatest likelihood of (e.g., having the strongest correlation with) an indication of present or impending worsening heart failure. In a similar manner, the numerically lowest weight corresponds to the type of information detected which points towards the least likelihood of (e.g., having the weakest correlation with) the indication of present or impending worsening heart failure. In one example, one or more of the weights are used in one or more algorithms to increase a sensitivity or specificity of the indication of present or impending worsening heart failure. In another example, the weights are obtained from historical information of one or more subjects previously found to have experienced heart failure.

In various examples, the system 100 includes a regimen control circuit 244 configured for initiating or adjusting a regimen (e.g., a therapy) to the subject 110 using, at least in part, information about at least one of the detected respiration disturbance, the detected arousal from stable state occurrence, or the determined indication of present or impending worsening heart failure. In one example, such regimen includes electrical stimulation, such as cardiac pacing, resynchronization, cardioversion or defibrillation stimulation, or neuromodulation, generated by a pulse generator circuit 246 and delivered via electrodes 250 selected by an electrode configuration switch circuit 248. The electrodes 250 are selected individually or simultaneously to serve as an anode or a cathode in any unipolar, bipolar or multipolar configuration.

In another example, such regimen is provided elsewhere (e.g., communicated to the nearby external user-interface 120 or delivered via an implantable drug pump 252) and includes, for example, a drug dose, a diet regimen, or a fluid intake regimen. In one example, the drug dose may include a set of one or more drug regimen instructions communicated and displayed on the external user-interface 120, and more specifically the user-detectable indication 124. In certain examples, the set of drug regimen instructions includes a suggested daily intake schedule of one or more drugs, such as diuretics, angiotensin-converting enzyme (ACE) inhibitors, beta blockers, digitalis, vasodilators, or the like. Alternatively, the drug dose may be automatically delivered per the suggested daily intake schedule via the implantable drug pump 252 or another drug dispensing device provided within the IMD 102 or implanted nearby and coupled thereto.

In a similar manner, the diet regimen and the fluid intake regimen may be communicated to the subject 110 via the user-detectable indication 124 of the external user-interface 120. In one example, the diet regimen may include a set of one or more dietary instructions to be followed by the subject 110, such as restriction of sodium to 2 grams or less per day and no more than one alcoholic drink per day. In another example, the fluid intake regimen may include a set of one or more fluid intake instructions to be followed by the subject 110, such as to avoid consuming an excessive amount of fluid. It is to be noted that FIG. 2 illustrates just one conceptualization of various modules, devices, circuits, and interfaces of the system 100, which are implemented either in hardware or as one or more sequences of steps carried out on a microprocessor or other controller. Such modules, devices, circuits, and interfaces are illustrated separately for conceptual clarity; however, it is to be understood that the various modules, devices, circuits, and interfaces of FIG. 2 need not be separate embodiments, but may be combined or otherwise implemented.

Figure 3:
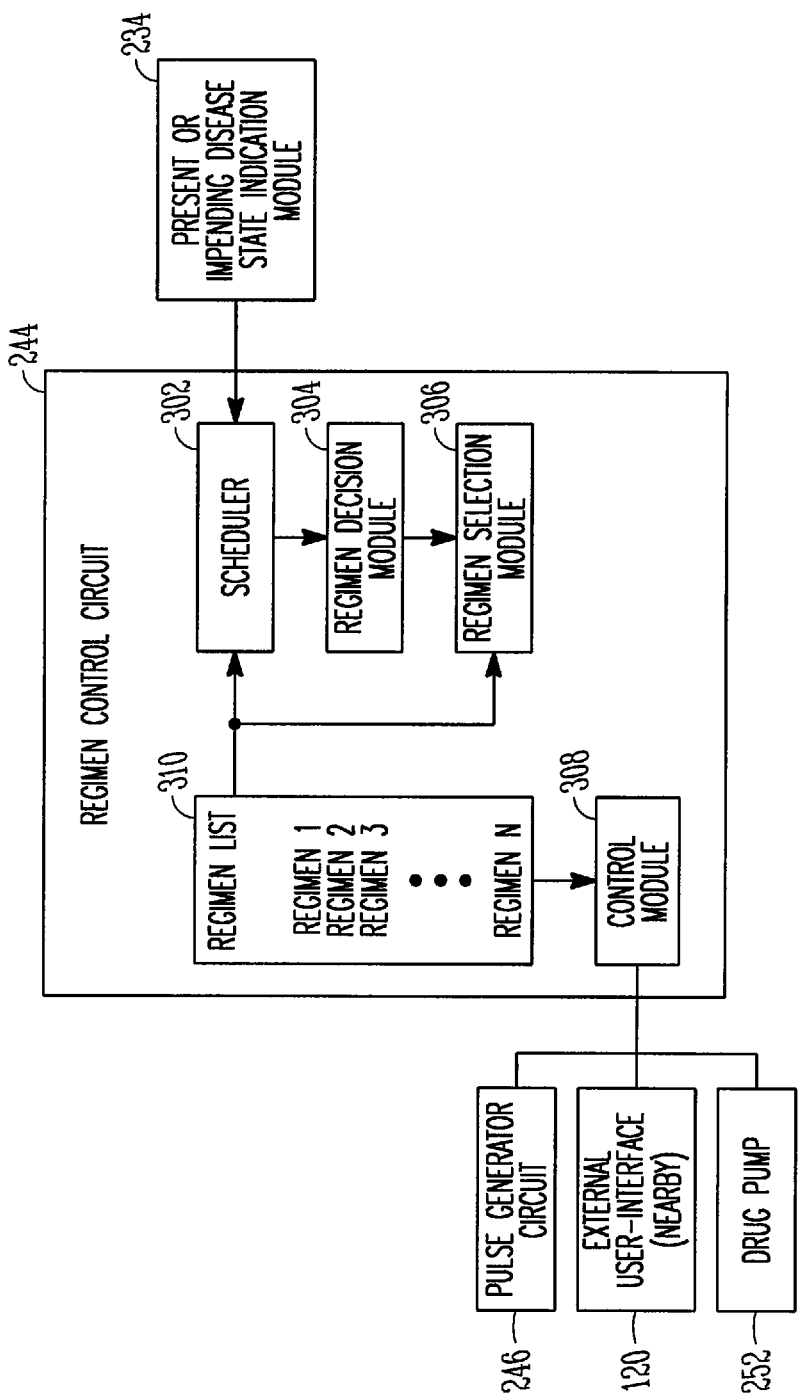
FIG. 3 is a block diagram illustrating one conceptual example of a regimen control circuit.

FIG. 3 is a block diagram illustrating one conceptual example of a regimen control circuit 244, which may be used to trigger one or more regimens (e.g., therapies) to a subject 110 (FIG. 1) in response to information about at least one of a detected respiration disturbance, a detected arousal from stable state occurrence, or a determined indication of present or impending worsening heart failure. The regimen control circuit 244 includes an input that receives an indication of present or impending worsening heart failure output from a present or impending disease state indication module 234. In one example, a scheduler 302 schedules the indications of present or impending worsening heart failure. A regimen decision module 304 decides whether some form of regimen is warranted. If a regimen is deemed to be warranted, a regimen selection module 306 selects one or more appropriate regimens. A control module 308 adjusts the selected regimen via an output to one or more of a pulse generator circuit 246, a nearby external user-interface 120, or a drug pump 252, for example.

The regimen control circuit 244 further includes a regimen list 310, which may include means to relate the regimens of the list 310 to the highest contributor(s) to the indication or present or impending worsening heart failure. In one example, the regimen list 310 includes all possible disease state preventive regimens or secondarily related regimens that the present system 100 (FIG. 1) may deliver or communicate to the subject 110. The therapy list 310 may be programmed into an IMD 102 (FIG. 2) either in hardware, firmware, or software and stored in a memory 226 (FIG. 2). In another example, the regimen list 310 includes immediate, short-term, intermediate-term, or long-term heart failure preventive therapies. Immediate heart failure preventive therapies include, by way of example, initiating or changing a drug dose administered to the subject via an implantable drug pump 252 or electrical stimulation administered to the subject 110 via the pulse generator circuit 246. Short-term heart failure preventive regimens include, by way of example, administering a continuous positive air pressure ("CPAP") dose to the subject 110 or notifying a caregiver to initiate or change the subject's drug dose treatment program. Intermediate-term heart failure preventive regimens include, by way of example, adjusting the subject's 110 lifestyle such as his/her diet or fluid intake regimen. Finally, long-term heart failure preventive regimens include, by way of example, notifying the subject 110 or caregiver to alter the drug which takes longer to affect the subject (e.g., beta blockers, ACE inhibitors) or administering CRT to the subject 110.

Each member of the regimen list 310 may be associated with a required time of action, which includes one or more of a time for the regimen to become effective or a time after which the regimen is no longer effective. In one example, only one member of the regimen list 310 is invoked at any particular time. In another example, combinations of different regimens are provided at substantially the same time. The various submodules in the regimen control module 244 are illustrated as such for conceptual purposes only; however, these submodules may alternatively be incorporated in the present or impending disease state indication module 244 or elsewhere.

Figure 4:
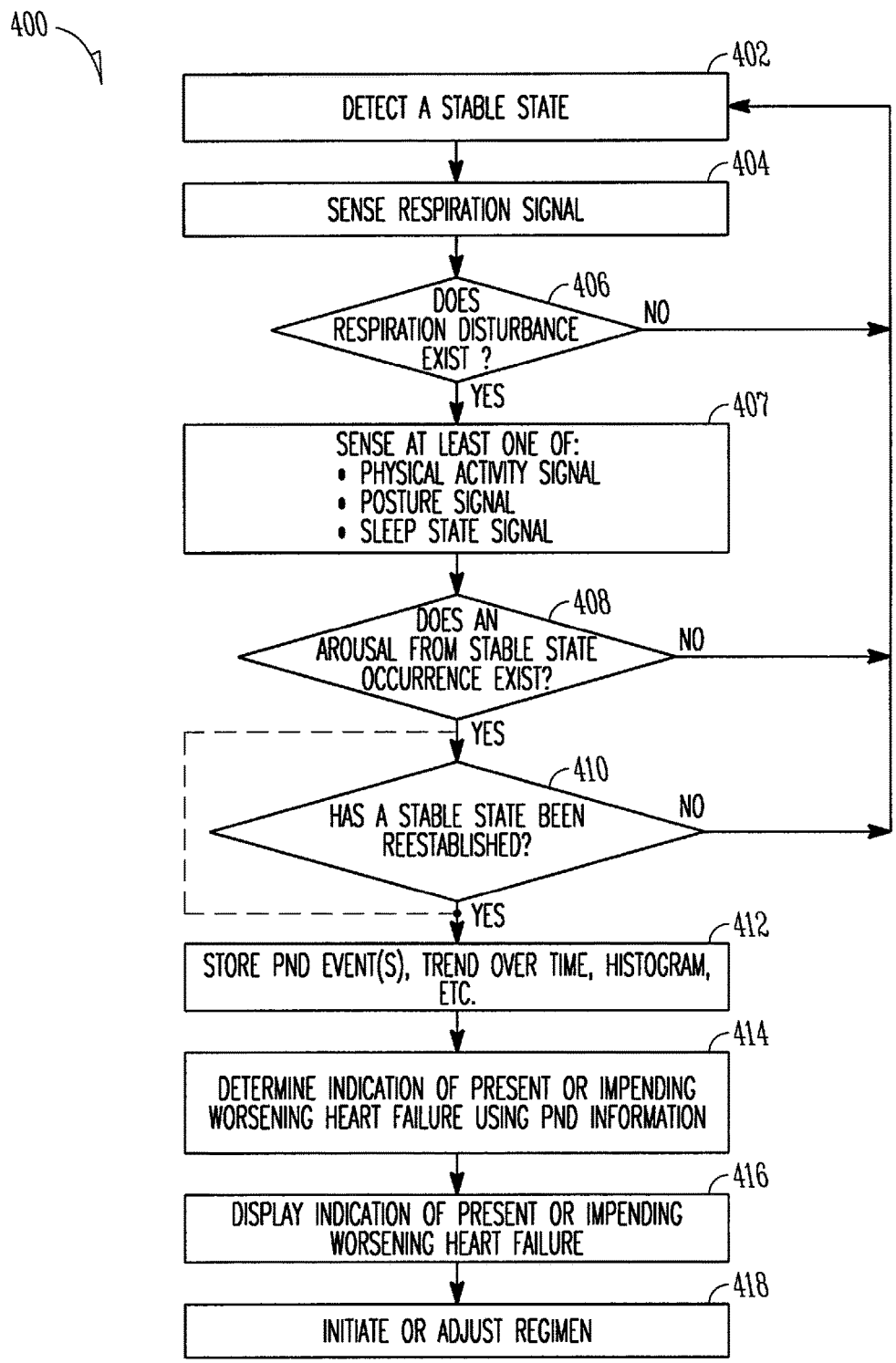
FIG. 4 is a chart illustrating one conceptual method of objectively diagnosing one or more respiration distress manifestations, such as one or more PND events.

FIG. 4 is a chart illustrating one conceptual method 400 of objectively diagnosing one or more respiration distress manifestations, such as one or more PND events. At 402, a stable state, such as at least one of a stable sleep state, a stable physical activity level, or a stable posture position, is detected. In one example, the stable sleep state is detected by a sleep detector circuit, such as is described in commonly-owned Carlson et al., U.S. patent application Ser. No. 09/802,316, entitled "CARDIAC RHYTHM MANAGEMENT SYSTEM USING TIME-DOMAIN HEART RATE VARIABILITY INDICIA." In another example, the stable physical activity level is detected by a physical activity sensor circuit in conjunction with a clock circuit that tracks the amount of time a subject maintains the steady physical activity level. In another example, the stable posture position is detected by a posture sensor circuit in conjunction with a clock circuit that tracks the amount of time a subject maintains the steady posture position. In various examples, a stable sleep state, a stable physical activity level, or a stable posture position is recorded when one of sleep or no physical activity or posture change, respectively, is detected for a 1-2+ hour time period. In other examples, a stable state is detected when one of sleep or no physical activity or posture change is detected for a 30 minute time period.

At 404, a respiration signal(s) indicative of a respiration or respiration related parameter (e.g., respiration rate, tidal volume, heart rate, or heart rate variability) of the subject is implantably sensed by a respiration sensor circuit. In one example, the respiration sensor circuit includes means for monitoring trans-thoracic impedance variation during each of the subject's inhale and exhale cycles to peak-detect, level-detect, or otherwise detect impedance variations resulting from breathing. In various other examples, the respiration signal information can be obtained from other signals or sources, such as from a blood pressure signal, a heart sound signal, or any other suitable sensor. At 406, it is determined whether a respiration disturbance, such as tachypnea (i.e., high respiration rate), decaying lung volume oscillations or an increase in periodic breathing (e.g., hypoventilation or hyperventilation), has been detected using the sensed respiration signal(s). If no respiration disturbance has been detected, the process returns to sensing a respiration signal(s) at 404.

If a respiration disturbance has been detected, the process continues to 407, where at least one of a physical activity signal(s) indicative of a physical activity level of the subject is implantably sensed by a physical activity sensor circuit, a posture signal(s) indicative of a posture of the subject is implantably sensed by a posture sensor circuit, or a sleep state signal(s) indicative of a sleep state of the subject is implantably sensed by a sleep state detector circuit. In one example, the physical activity sensor circuit includes an accelerometer, such as a single axis accelerometer or a multi-axis accelerometer. In another example, the posture sensor circuit includes at least one of a tilt switch, a single axis accelerometer, or a multi-axis accelerometer, the latter of which allows a detectable signal to be produced regardless of the orientation of the subject's body. At 408, it is determined whether the respiration disturbance has been followed by an associated arousal from stable state occurrence, such as an increase in physical activity or a change in the subject's posture to a more upright position including both standing and sitting orientations, using the sensed physical activity signal(s) or the posture signal(s). If the respiration disturbance is not followed by an associated arousal from stable state occurrence, the process returns to detecting one of a stable sleep state, a stable physical activity level, or a stable posture position at 402.

If the respiration disturbance is followed by an associated arousal from stable state occurrence, the process continues to 412, where a PND event is stored and evaluated, such as trended or counted, over time, or optionally to 410, where it is first determined whether a stable sleep state, a stable physical activity level, or a stable posture position has been reestablished. In one example, a return to a stable state after a positive indication of an arousal verifies that a respiration distress manifestation, such as a transitory PND event, has actually occurred. At 414, an indication of present or impending worsening heart failure is determined using, at least in part, the evaluated information over time of one or both of the respiration disturbance or the associated arousal from stable state occurrence. At 416, the indication of present or impending worsening heart failure is displayed to the subject or his/her caregiver, such as via a user-detectable indication integrated with an external user-interface. At 418, a regimen is initiated or adjusted in response to the indication of present or impending worsening heart failure.

Figure 5:
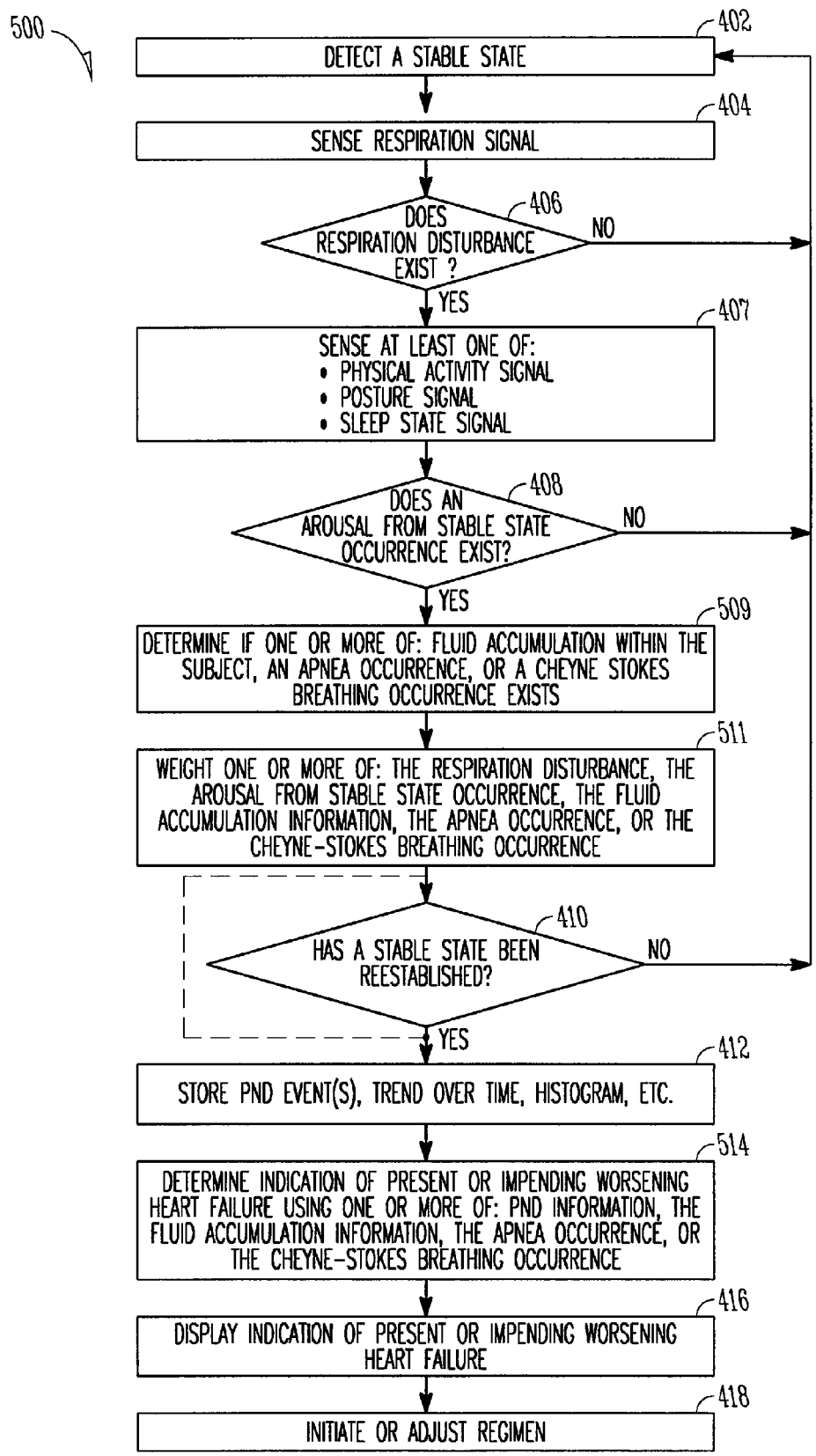
FIG. 5 is a chart illustrating another conceptual method of objectively diagnosing one or more respiration distress manifestations, such as one or more PND events.

FIG. 5 is a chart illustrating another conceptual method 500 of objectively diagnosing one or more respiration distress manifestations, such as one or more PND events. The method 500 of FIG. 5 is similar to the method 400 of FIG. 4, with the exception that at 509, at least one of fluid accumulation within the subject, an apnea occurrence experienced by the subject, or a Cheyne-Stokes breathing occurrence experienced by the subject is detected, and optionally at 511, weighted with one or both of the respiration disturbance or the associated arousal from stable state occurrence. Then, at 514, the indication of present or impending worsening heart failure is determined using not only the evaluated information over time of one or both of the respiration disturbance or the associated arousal from stable state occurrence, but also information about at least one of the fluid accumulation with the subject, the apnea occurrence experienced by the subject, or the Cheyne-Stokes breathing occurrence experienced by the subject.

CONCLUSION

Today, CHF is a major cause of hospital admissions. It is estimated that approximately 30-40% of subjects with CHF—currently approximately 500,000 people in the United States alone—are hospitalized every year. A portion of these admissions is due to excessive fluid build-up collecting in, or flowing to, a subject's thorax, thereby becoming a barrier to normal gas exchange and causing respiration distress. The fluid build-up in the thorax may result in pulmonary edema or pleural effusion, both of which can be challenging to treat and often go unrecognized until a subject is critically ill.

Advantageously, the present system and methods provide for the timely, objective diagnosis of one or more respiration distress manifestations, such as one or more PND events, by implantably recognizing their occurrence and evaluating information over time about the same as an indication of present or impending worsening heart failure. Using an implantable respiration sensor circuit, an implantable physiological sensor circuit, such as at least one of a physical activity sensor circuit or a posture sensor circuit, and optionally a fluid detector circuit, an apnea detector circuit, or a Cheyne-Stokes breathing detector circuit, PND or other respiration manifestation events can be evaluated, such as trended or counted, over time for use as an indication of present or impending worsening heart failure. Using information about one or more PND events may advantageously provide a tool for early, and therefore actionable, detection to present or impending worsening heart failure.

It is to be understood that the above Detailed Description is intended to be illustrative, and not restrictive. For instance, any of the aforementioned examples may be used individually or with any of the other examples. Many other examples may be apparent to those of skill in the art upon reviewing the above description. As one example, the present systems and methods may be used to objectively diagnose other respiration manifestations, such as an orthopnea event (i.e., discomfort in breathing that is relieved by an arousal event, such as sitting or standing in an erect position), and use information about such diagnosis to provide an indication of present or impending worsening heart failure. Therefore, the scope of the present systems and methods should be determined with reference to the appended claims, along with the full scope of legal equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, assembly, article, or process that includes elements in addition to those listed after such a term in a claim are still deemed to fall within the scope of such claim.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims.

What is claimed is:

1. A system comprising:
    an implantable medical device including,
        a respiration sensor circuit configured for producing a respiration signal indicative of a respiration or a respiration related parameter of a subject; and
        a physiological sensor circuit that includes at least one of a physical activity sensor circuit configured for producing a physical activity signal indicative of a physical activity level of the subject or a posture sensor circuit configured for producing a posture signal indicative of a posture of the subject; and
    an implantable or external processor circuit including an input to receive information about the respiration signal and at least one of the physical activity signal or the posture signal, the processor circuit configured for detecting a paroxysmal nocturnal dyspnea (PND) event by detecting a respiration disturbance using the respiration signal and detecting an associated subsequent arousal from stable state occurrence caused by the respiration disturbance, from at least one of the physical activity signal or the posture signal, the processor circuit further configured for evaluating over time, at least in part, the respiration disturbances and the associated subsequent arousal from stable state occurrences caused by the respiration disturbance by comparing a trend or count of the respiration disturbances and the associated arousal from stable state occurrences to a specified threshold, providing an indication of present or impending worsening heart failure.

2. The system of claim 1, comprising a clock circuit configured for producing at least one timestamp associated with at least one of the respiration signal, the physical activity signal, or the posture signal.

3. The system of claim 2, comprising a memory configured for storing information about the timestamp and at least one of the respiration signal, the physical activity signal, or the posture signal with which the timestamp is associated.

4. The system of claim 1, comprising a regimen control circuit configured for adjusting a regimen provided to the subject using, at least in part, information about at least one of the detected respiration disturbance, the detected arousal from stable state occurrence, or the indication of present or impending worsening heart failure.

5. The system of claim 1, comprising an external user-interface device communicatively coupled to the implantable medical device and including a user-detectable indication of an evaluation over time of at least one of the respiration disturbance, the arousal from stable state occurrence, or the indication of present or impending worsening heart failure.

6. The system of claim 5, wherein the external user-interface device includes a user input device configured for receiving programming information from a user and communicating the programming information to the implantable medical device.

7. The system of claim 1, comprising a fluid detector circuit configured for producing an indication of a fluid level within the subject; and wherein the processor circuit is configured to receive the indication of the fluid level for use in determining the indication of present or impending worsening heart failure.

8. The system of claim 7, wherein the fluid detector circuit includes an external weight scale comprising a communication circuit configured for directly or indirectly communicating fluid level information to the processor circuit.

9. The system of claim 1, comprising a stable state detector including at least one of a sleep detector circuit configured for determining whether the subject is asleep or awake, the physical activity sensor, or the posture sensor.

10. The system of claim 1, wherein the respiration sensor circuit is configured to produce the respiration signal in response to a detected change in a fluid level within the subject.

11. The system of claim 1, wherein the respiration sensor circuit is configured to produce the respiration signal in response to a detected change in lung volume.

12. The system of claim 1, wherein the respiration sensor circuit is configured to produce the respiration signal in response to a detected change in respiration rate.

13. The system of claim 1, wherein the respiration signal produced by the respiration sensor circuit includes information about at least one of a respiration rate, a tidal volume, a heart rate, or a heart rate variability.

14. The system of claim 1, wherein the physical activity sensor circuit is configured to produce the physical activity signal in response to a detected increase in the physical activity level.

15. The system of claim 1, wherein the posture sensor circuit is configured to produce the posture signal in response to a detected change in the posture to a more upright position.

16. The system of claim 1, wherein the processor circuit includes a trending module configured to trend information about one or both of the respiration disturbance or the associated subsequent arousal from stable state occurrence.

17. The system of claim 1, wherein the processor circuit includes a counter module configured to count the prevalence over time of one or both of the respiration disturbance or the associated subsequent arousal from stable state occurrence.

18. The system of claim 1, including an apnea detector circuit to produce information about an apnea occurrence.

19. The system of claim 1, including a Cheyne-Stokes breathing detector circuit to produce information about a Cheyne-Stokes breathing occurrence.

20. The system of claim 1, further comprising a regimen control circuit configured for adjusting a regimen provided to the subject using, at least in part, information about at least one of the detected respiration disturbance, the detected arousal from stable state occurrence, or the indication of present or impending worsening heart failure, wherein the regimen includes electrical stimulation.

* * * * *